United States Patent
Samadpour

(10) Patent No.: US 9,957,475 B2
(45) Date of Patent: May 1, 2018

(54) MICROBIAL SAMPLING DEVICE

(75) Inventor: Mansour Samadpour, Seattle, WA (US)

(73) Assignee: Institute for Environmental Health, Inc., Lake Forest Park, WA (US)

(*) Notice: Subject to any disclaimer, the term of this patent is extended or adjusted under 35 U.S.C. 154(b) by 1498 days.

(21) Appl. No.: 10/584,098

(22) PCT Filed: Dec. 22, 2004

(86) PCT No.: PCT/US2004/043254
§ 371 (c)(1),
(2), (4) Date: Oct. 30, 2007

(87) PCT Pub. No.: WO2005/062914
PCT Pub. Date: Jul. 14, 2005

(65) Prior Publication Data
US 2008/0166752 A1    Jul. 10, 2008

Related U.S. Application Data

(60) Provisional application No. 60/531,364, filed on Dec. 22, 2003.

(51) Int. Cl.
*C12M 1/34* (2006.01)
*C12Q 1/20* (2006.01)
(Continued)

(52) U.S. Cl.
CPC .......... *C12M 41/36* (2013.01); *C12M 37/00* (2013.01); *G01N 1/02* (2013.01); *G01N 2001/028* (2013.01); *G01N 2001/383* (2013.01)

(58) Field of Classification Search
CPC .......... G01N 1/02; G01N 2001/383; G01N 2001/028; G01N 1/22; G01N 1/14;
(Continued)

(56) References Cited

U.S. PATENT DOCUMENTS 4,038,057 A    7/1977 Roth
6,013,227 A *  1/2000 Lin .................... A61L 2/186
                                                422/28
(Continued)

FOREIGN PATENT DOCUMENTS

WO    WO 2004/098296    11/2004

OTHER PUBLICATIONS

"Media Index," U.S. Food and Drug Administration, Bacteriological Analytical Manual Online, retrieved from http://www.cfsan.fda.gov/~ebam/bam-4.html. on Jun. 17, 2008.

*Primary Examiner* — William H Beisner
*Assistant Examiner* — Danielle Henkel
(74) *Attorney, Agent, or Firm* — Barry L. Davison; Davis Wright Tremaine LLP

(57) ABSTRACT

Aspects of the present invention provide novel apparatus and methods for sampling microbial organisms present on surfaces. Preferred apparatus comprises: a reservoir suitable for providing microbial collection fluid; a sterilizable sample collection chamber; a sterilizable, integrated collection fluid delivery and collection fluid recovery member, suitable to deliver collection fluid to a target surface, and contemporaneously recover the delivered fluid from the surface; delivery means, in communication with both the reservoir and the integrated member, and operable to aseptically deliver collection fluid from the reservoir to the integrated member; and vacuum means, in communication with both the sample collection chamber and the integrated member, and operable to direct collection fluid, delivered and recovered by the integrated member, to the sample collection chamber. Additional aspects provide a method for rapid, high-throughput sampling of microbial organisms present on surfaces, comprising: delivering sample collection fluid to a target surface, and contemporaneously recovering the delivered fluid from the target surface by means of an integrated collection fluid delivery and collection fluid recovery member; and collecting the recovered sample collection fluid into a sample (Continued)

collection chamber in communication with the integrated member, whereby sample collection is, at least in part, achieved. The inventive methods and apparatus can be applied to both surface sampling and to atmospheric sampling.

18 Claims, 5 Drawing Sheets

(51) Int. Cl.
  *G01N 1/02* (2006.01)
  *C12M 1/12* (2006.01)
  *G01N 1/38* (2006.01)

(58) Field of Classification Search
  CPC ..... G01N 2001/024; G01N 2001/1043; G01N 2001/2071; G01N 2035/00277; G01N 33/1826; G01N 33/18; G01N 1/2226; G01N 2015/0088; G01N 2015/0092; G01N 15/0618
  USPC ...................................................... 435/309.1
  See application file for complete search history.

(56) References Cited

U.S. PATENT DOCUMENTS

| | | | |
|---|---|---|---|
| 6,240,768 B1 | 6/2001 | Lemmonnier | |
| 6,338,282 B1* | 1/2002 | Gilbert | 73/864.34 |
| 6,472,203 B1 | 10/2002 | Gallup et al. | |
| 2004/0107782 A1* | 6/2004 | Bradley et al. | 73/864.34 |
| 2006/0060006 A1* | 3/2006 | Ornath et al. | 73/864.33 |

* cited by examiner

SANITIZING UNIT

MICROBIAL SAMPLING DEVICE

CROSS REFERENCE TO RELATED APPLICATIONS

This application is the United States national phase application, under 35 U.S.C. § 371, of International Patent Application No. PCT/US2004/043254, filed Dec. 22, 2004, entitled "MICROBIAL SAMPLING DEVICE," which claims the benefit of U.S. Provisional Patent Application No. 60/531,364, filed Dec. 22, 2003, entitled "VACUUM SAMPLE COLLECTOR," both of which are incorporated by reference herein in their entireties.

FIELD OF THE INVENTION

Preferred aspects of the present invention relate generally to collecting samples of microbial agents, and particularly to improving the efficiency of collecting representative and reproducible samples of microbial agents on surfaces, and from air.

BACKGROUND OF THE INVENTION

Determination and monitoring of the microbial load on a variety of surfaces is often highly desirable. In the environmental field, for example, collection of surface and air samples for microbiological analysis poses a significant challenge. Likewise, food surfaces in the food industry, such as food contact surfaces, and non-food contact surfaces all represent points of microbial harborage or opportunities for cross-contamination. An example of a typical food surface is an animal carcass surface. At present, carcass surfaces are most commonly sampled either using moistened sponges, or by excising a thin portion of the surface using a knife. While both of these prior art devices and methods have numerous laudable benefits, they have a multiple shortcomings that detract from utility.

Sponge sampling, for example, requires execution of a prolonged series of procedural steps to ensure that the sampling media: is aseptically extracted from its packaging prior to use; is applied to the surface in a way that collects microbial contamination in a representative manner; and is returned to the packaging in such a way as to prevent cross-contamination and loss of sample integrity. Variations in technique, such as pressure during application, number of 'passes,' and/or whether or not an 'area template' is used, can result in an undesirable level of variable results.

Likewise, excision sampling requires execution of a prolonged series of procedural steps to ensure that the instruments used to excise the sample are sterile, and that a portion of the sample is excised in a way that collects microbial contamination in a representative manner, and that the sample is packaged in such a way as to prevent cross-contamination and loss of sample integrity. Moreover, removal of a portion of the surface by excision can be detrimental to the aesthetic quality and desirability of the food product. Furthermore, variations in the depth and technique of the excision can lead to a greater or lesser mass of food product being included in the sample, thereby making it difficult to interpret and normalize the data in terms of microbial contamination per unit surface area.

Additionally, it is often desirable to form a composite sample for the purposes of determining an average value for a microbial determinant of interest. In this instance, because methods such as sponge and excision sampling collect unit samples, additional effort must be expended to combine multiple samples to form one composite sample. Such additional effort can require significant time, and increase the probability that procedural errors (e.g., cross-contamination and/or miscounting) will be introduced.

Therefore, there is a pronounced need in the art for less labor intensive methods of microbial sampling of surfaces including, but not limited to food surfaces, food contact surfaces, and non-food contact surfaces.

There is a pronounced need in the art for more accurate methods of microbial sampling of surfaces which reduce variations in the manner in which samples are collected, thereby reducing overall errors in the results.

There is a pronounced need in the art for methods of microbial sampling of surfaces that facilitate the collection of composite samples, shortening the time required, and reducing the errors otherwise associated with the formation of the composite sample.

There is a pronounced need in the art for non-invasive methods of microbial sampling of food surfaces which are less detrimental to the aesthetic quality and desirability of the food product.

SUMMARY OF THE INVENTION

Preferred aspects of the present invention provide a device and method, which can be used for air sampling as well as for surface sampling.

Additional preferred aspects of the present invention provide a universal sampling device and methods for using same, allowing repeated aseptic sampling of microbial agents on surfaces and from air. Particularly preferred aspects provide for integrated sanitization of the sampling unit between sampling runs or events.

Specific aspects provide improved devices and methods for conducting microbial sampling of surfaces including food surfaces, food contact surfaces, and non-food contact surfaces.

Particular aspects provide a device which reduces the number of procedural steps required to conduct microbial sampling of surfaces.

Additional preferred aspects provide a device that collects microbial contamination with a high efficiency.

Further aspects provide a device and method, which reduces the variation in sample collection, thereby reducing the variation and error in the results.

Yet further aspects provide a device which yields results that can be correlated with historical data.

Particularly preferred aspects provide a device which does not degrade the aesthetic quality and desirability of the surface being sampled.

Additional aspects provide a device which can be used for collection of single discrete samples.

In preferred aspects, the inventive devices 'self-sanitize' for repeated sampling.

Particularly preferred aspects provide a device which facilitates the collection of a composite sample, representing the sum of several single discrete samples.

These, as well as other objectives, are accomplished by an apparatus which impinges an appropriate microbial sampling fluid upon a surface to be sampled, and then recovers the fluid to a reservoir for subsequent analysis. The apparatus comprises a reservoir of an appropriate microbial sampling fluid. By pressurizing the reservoir, or by action of a pump, an appropriate quantity of the fluid is delivered and dispersed onto the surface to be sampled (e.g., by spray delivery through a nozzle). The fluid entrains any microbial contamination that may be present, and is then recovered by application of a vacuum to the targeted surface, drawing the fluid from the surface and directing it to a collection reservoir. The contents of the reservoir are emptied after a single sample, or, optionally after multiple samples have been collected in forming one composite sample.

Preferably, a nozzle delivering the microbial sampling fluid is incorporated into a sampling head. The sampling head may have a well-defined geometry, such as a rectangular configuration, which facilitates/complements the collection of a sample from a known surface area.

Specific preferred embodiments of the present invention provide an apparatus for sampling microbial organisms present on surfaces, comprising: a reservoir suitable for providing microbial collection fluid; a sterilizable sample collection chamber; a sterilizable, integrated collection fluid delivery and collection fluid recovery member, suitable to deliver collection fluid to a target surface, and contemporaneously recover the delivered fluid from the surface; delivery means, in communication with both the reservoir and the integrated member, and operable to aseptically deliver collection fluid from the reservoir to the integrated member; and vacuum means, in communication with both the sample collection chamber and the integrated member, and operable to direct collection fluid, delivered and recovered by the integrated member, to the sample collection chamber.

Preferably, the integrated fluid delivery and recovery member is reversibly detachable. Preferably, the reservoir is a pressurizable chamber. Preferably, the delivery means comprises a compressor in communication with the chamber. Alternatively, the delivery means comprises a fluid pump. Preferably, the vacuum means comprises a vacuum pump, and a moisture trap interposed between the sample collection chamber and the vacuum pump. Preferably, the integrated collection fluid delivery and collection fluid recovery member, comprises a spray nozzle suitable to direct sample collection fluid toward the target surface. Preferably, the integrated collection fluid delivery and collection fluid recovery member comprises a actuatable valve for actuated delivery of the sample collection fluid.

Preferably the sampling apparatus further comprises a sanitizing means for sanitizing the integrated collection fluid delivery and collection fluid recovery member. Preferably, the sanitation means comprises a sanitation unit having a sanitizing reservoir for receiving the integrated collection fluid delivery and collection fluid recovery member.

In preferred aspects, the integrated collection fluid delivery and collection fluid recovery member conforms to the target surface contour. Preferably, the shape or size of the integrated collection fluid delivery and collection fluid recovery member is calibrated to facilitate sample collection from a predetermined target surface area.

Additional embodiments provide a method for rapid, high-throughput sampling of microbial organisms present on surfaces, comprising: delivering sample collection fluid to a target surface, and contemporaneously recovering the delivered fluid from the target surface by means of an integrated collection fluid delivery and collection fluid recovery member; and collecting the recovered sample collection fluid into a sample collection chamber in communication with the integrated member, whereby sample collection is, at least in part, achieved.

Preferably, the target surface is a food surface or a food-contact surface. Preferably, the food surface is that of an animal or animal carcass. Preferably, the animal carcass is bovine, porcine, equine or avian. Preferably, the microbial collection fluid preserves microbial vitality without promoting microbial growth, allowing for determination of microbial number per unit surface area. Alternatively, the microbial collection fluid promotes microbial growth, allowing for determination of a presence of absence of surface microbial organisms.

Particularly preferred aspects of the present invention comprise combining the instant inventive surface sampling methods with the advanced pathogen testing and carcass-certification methods for slaughter operations described in WO04098296A2, which is incorporated by reference herein in its entirety.

Further aspects provide a method for rapid, high-throughput atmospheric sampling of microbial organisms, comprising: collecting an atmospheric sample by means of an integrated collection fluid delivery and collection fluid recovery member, the integrated member in communication with vacuum means; and directing the collected atmospheric sample into an impinger comprised of a sample collection chamber having a diffuser tube, whereby atmospheric sampling of microbial organisms is, at least in part, provided.

DETAILED DESCRIPTION OF THE INVENTION

Figure 1:
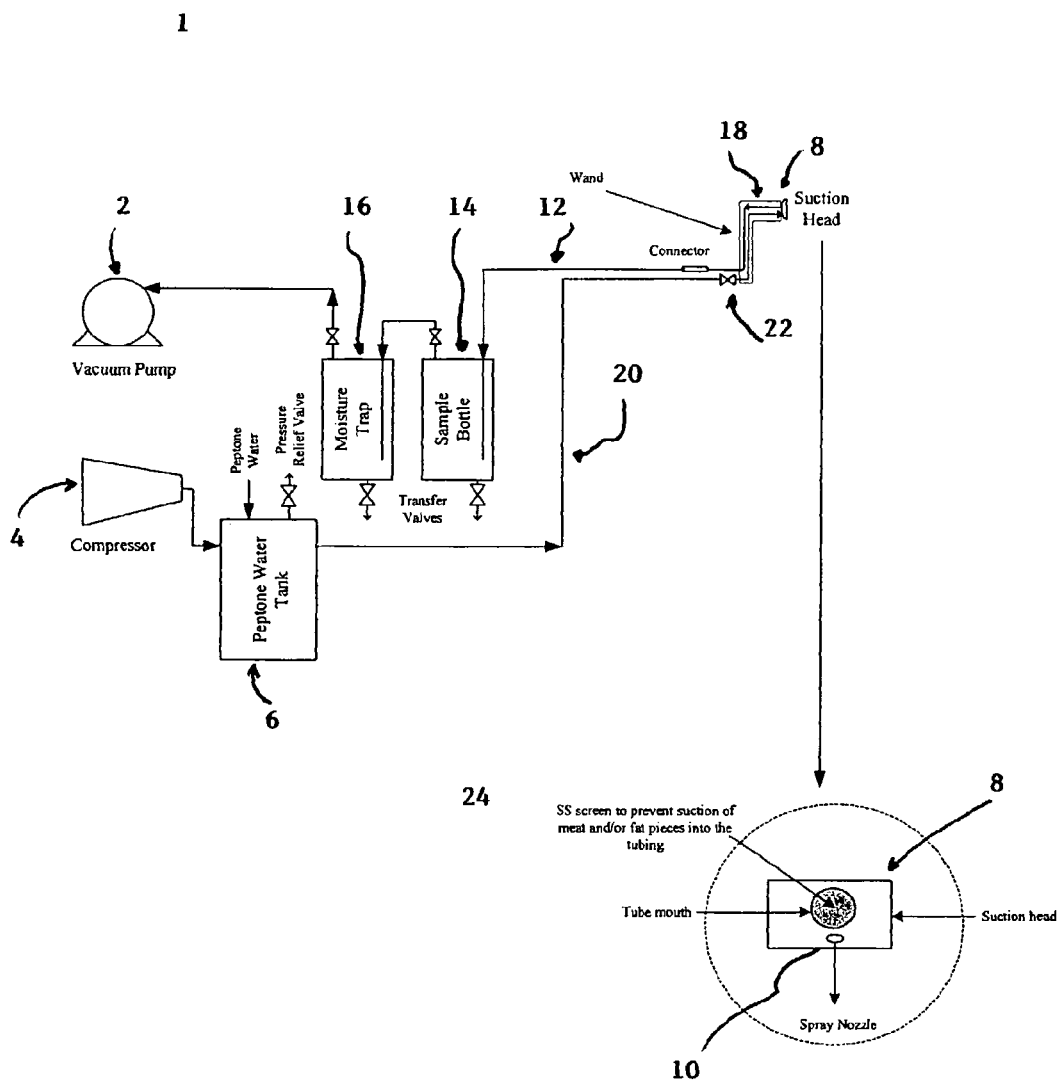
FIG. 1 shows a schematic diagram of a preferred embodiment of the invention, illustrating the use of a compressor to pressurize peptone water, a microbial sampling fluid, for delivery through a nozzle contained in a sampling wand/head. The sampling fluid is collected in a sample bottle by means of applying a vacuum.
Figure 2:
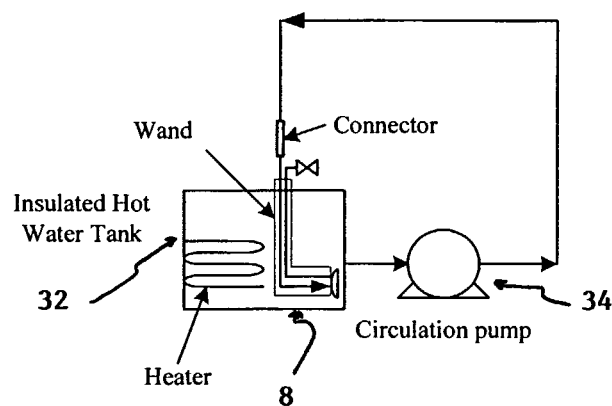
FIG. 2 shows a schematic diagram of an exemplary sanitizing unit used to prepare (e.g., sanitize) a sampling wand before and between collection of samples.

Referring more particularly to the drawings, an exemplary embodiment of the present invention is best understood by reference to FIGS. 1 and 2. Preferably, an exemplary inventive sampling device 1 comprises a vacuum pump 2, a compressor 4, a pressurized tank 6 containing microbial sampling fluid, a vacuum application/suction head 8 containing a nozzle 10 for the application of the microbial sampling fluid, a vacuum hose 12 for returning the applied sampling fluid to a sample bottle 14, and a moisture trap 16 for protecting the vacuum pump 2.

Alternatively the compressor 4 and pressurized tank 6 could be replaced, for example, with a non-pressurized tank in communication with a pump operable to deliver sampling fluid from the tank to the nozzle 10 of the application/suction head 8.

The principle operation of this preferred embodiment of the invention is to direct (e.g., spray) microbial sampling fluid onto the surface to be sampled, and then recover the liquid into a sample bottle 14 by means of, for example, application of a vacuum at the application/suction head 8.

Preferred microbial sampling solutions include those which preserve the viability of the organism without promoting growth. Samples based on such solutions can be returned to the laboratory and analyzed by standard plating techniques to determine the number of viable organisms per unit of recovered sampling solution. By measuring the total volume of recovered sampling solution, the total number of organisms recovered can be computed. By measuring the total surface area where the sampling device was applied, the number of viable organisms per unit of area can be computed.

Preferred microbial sampling solutions also include those which preserve the viability of the organism while promoting growth (so called "enrichment broths"). Samples based on these solutions can be returned to the laboratory and analyzed to determine the presence/absence of organisms of concern.

Appropriate microbial sampling solutions (including both enrichment and non-enrichement types) include, but are not limited to, those described standard liquid media such as those found in the media index of the "Bacteriological Analytical Manual" published by the U.S. Food and Drug Administration, Center for Food Safety and Applied Nutrition (1998, Edition 8, Revision A, and updates placed on the FDA/CFSAN internet site, designated the BAM online, with media revision dates through May, 2004).

Figure 3:
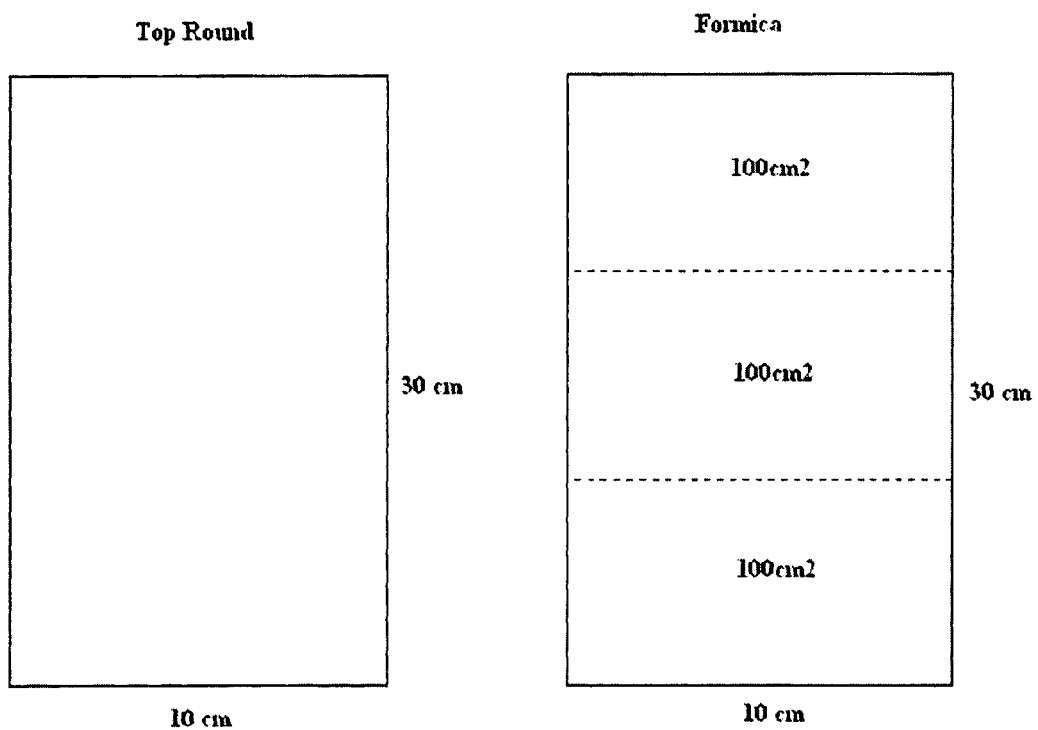
FIG. 3 shows a schematic diagram of a sampling pattern used during comparative experiments disclosed herein.

Preferably, the compressor 4 provides pressure to the pressure tank 6 that delivers the microbial sampling fluid to the spray nozzle 10 located inside the application/suction head 8 (integrated collection fluid delivery and collection fluid recovery member 8). The spray nozzle 10 directs the fluid onto the surface to be sampled, in a line approximately the width of the application/suction head 8. The rate of application, which along with the time of application affects the volume of fluid recovered per unit surface area, can be adjusted by modifying the pressure in the pressure tank 6. It is desirable, though not necessary, to use the minimum volume of fluid that is sufficient to remove the microbial organisms from the surface type being sampled.

Alternatively, a pump can be placed between the reservoir of the microbial sampling fluid and the application nozzle 10, and the rate of application can be adjusted by adjustment of the pump rate.

Preferably, the fluid is extracted from the surface being sampled by applying a vacuum through a flexible hose 12 terminating in a vacuum head (e.g., application/suction head 8) containing the spray nozzle 10. The microbial sampling fluid is extracted from the surface being sampled by vacuum, first through a wand (e.g., application/suction head 8), and then a hose 12 connecting the wand to the sample bottle. The wand handle 18 connecting the wand 8 and the sample hose 12 to the sample bottle 14 has, for example, a trigger design valve that controls delivery and/or amount of fluid delivered to the target surface. An optional screening means (e.g., stainless steel screen 24) may be used in the aspiration pathway to preclude aspiration of target substrate pieces. An optional moisture trap 16 between the sample bottle 14 and the vacuum pump 2 protects the vacuum pump from moisture.

Preferably, the shape of the integrated collection fluid delivery and collection fluid recovery member 8 (vacuum head) facilitates collection of a sample from a known sample area. For example, a rectangular head of dimensions 10 cm×5 cm would expedite collection of samples from a surface area of 100 $cm^2$, a common sample size, by drawing the sample head vertically the distance of two head depths (2×5=10 cm) and then horizontally a distance of two head depths across the same surface.

Preferably, all components are contained on a cart or other movable platform. The sampling bottle 14 and moisture trap 16 are preferably located in a accessible rack on top of the cart. Optimally, the rack has space for additional sample bottles. The vacuum pump 2, compressor 4, and pressure vessel 6 are preferably located on the enclosed bottom shelf. In particular embodiments, a double-door provides access to the equipment on the shelf.

The moisture trap 16, sample bottle 14, sample hose 12, and wand 8 can quickly be separated. Similarly, the various segments of the sampling solution supply line 20 supplying peptone water from the pressure tank 6 to the spray nozzle 10 in the suction head 8 are optionally connected by 'quick disconnects' 22.

Preferably, an optionally retractable electric cord that is located inside the covered portion of the cart supplies power to the unit. The vacuum pump 2 is optionally controlled by a switch on the cart side panel.

Preferably, a separate sanitizing unit 30 is constructed to allow the wand 8 to be sterilized before and/or between sampling events. The apparatus of the sanitizing unit 30 is best understood by reference to FIG. 2.

Preferably, the sanitizing unit 30 contains a sanitizing reservoir 32 of liquid (e.g., water) maintained at an elevated temperature (e.g., by a heater 36) sufficient to be lethal to microorganisms upon contact. The wand 8 with the vacuum tube 12 (or a detachable portion thereof) is removed from the sampling device 1, and each end is connected to the sanitizing unit 30 in such a fashion as to form a closed loop between the wand 8, the heated water reservoir 32 and a sanitizer pump 34. Activation of the pump 34 causes hot liquid (e.g., water) to be circulated through the wand 8, ensuring that all microbial organisms therein contained are killed. The wand 8 is returned to the sampling device 1, along with a fresh sterilized sampling bottle 14, and the sampling unit 1 is ready to collect another sample.

In an alternate preferred embodiment for atmospheric sampling, a diffuser tube is connected to the receiving hose in the collection chamber 14, which will convert the sampling device to an 'impinger,' allowing for quantitative air sampling. To complete the conversion, the collection chamber is partially filled with microbial sampling fluid. The same fluids that are impinged on a surface may be placed in the collection chamber. Impingers are well known in the art. Typically, they comprise special glass tubes designed to collect airborne contaminants by bubbling the sampled air at a high flow rate through a method specific absorbing liquid. The liquid used can then be analyzed to determine airborne contaminate levels. Traditionally, liquid-filled impingers have been preferred as devices for collecting bioaerosols. Liquid-filled impingers offer the advantage of easy microbial analysis because portions of the collection liquid can be placed directly onto nutrient media (agar), which is incubated and the resulting colonies enumerated and identified. Impingers are widely available, inexpensive, and sterilizable.

The foregoing description is provided to facilitate understanding of the invention in terms of its exemplary preferred embodiments. However, many variations of the invention, as will be appreciated by those of skill in the relevant art, may be made without departing from the spirit and scope of the invention, the breadth of which is more accurately reflected in the appended claims.

EXAMPLE 1

The exemplary apparatus 1 of FIG. 1 was compared to current art swab sampling methods for collection of a microbial sample from a meat surface. Meat surfaces were freshly prepared by thinly slicing a whole top round portion of beef using a sterilized knife. The internal tissue of such whole rounds is generally regarded as having a low microbial organism level. The freshly prepared surfaces were then inoculated at two different levels ($10^5$ and $10^4$ CFU/100 cm$^2$) with Biotype I *Escherichia coli* (ECC) prepared from known stock laboratory cultures in slurry of sterilized fecal matter. Surfaces were inoculated by spreading 10 mL of the slurry on a 300 cm$^2$ area of the surface to be sampled, according to the schematic provided in FIG. 3.

Swab samples were collected using sterile sponges moistened with 25 mL of 0.1% peptone water, according to standard methodology recommended by the United States Department of Agriculture (USDA), Food Safety and Inspection Services (FSIS). The apparatus 1 of FIG. 1 was used to collect comparative samples. The sampling fluid reservoir contained 0.1% peptone water, and a volume of approximately 25 mL was applied to the surface while simultaneously using the vacuum to recover the applied fluid. Sampling was done in quintuplicate (n=5). The ECC content of the collected samples was determined through standard serial dilution and plate counting methods. The results obtained with each method are listed below in TABLE 1:

TABLE 1

| Innoculation Level | Top Round Meat Surface | |
|---|---|---|
| (CFU/100 sq cm[1]) | Swab Sampling[2] | Invention |
| $10^5$ | 5.22 ± 0.25 | 5.53 ± 0.22 |
| $10^4$ | 3.88 ± 0.14 | 4.12 ± 0.07 |
| 0 | 0 | 0 |

[1]Surfaces were inoculated by spreading 10 mL of a fecal slurry containing the indicated CFU of Biotype I *Escherichia coli* (ECC).
[2]Results are reported as log base 10, plus or minus the standard deviation (n = 5).

Figure 4:
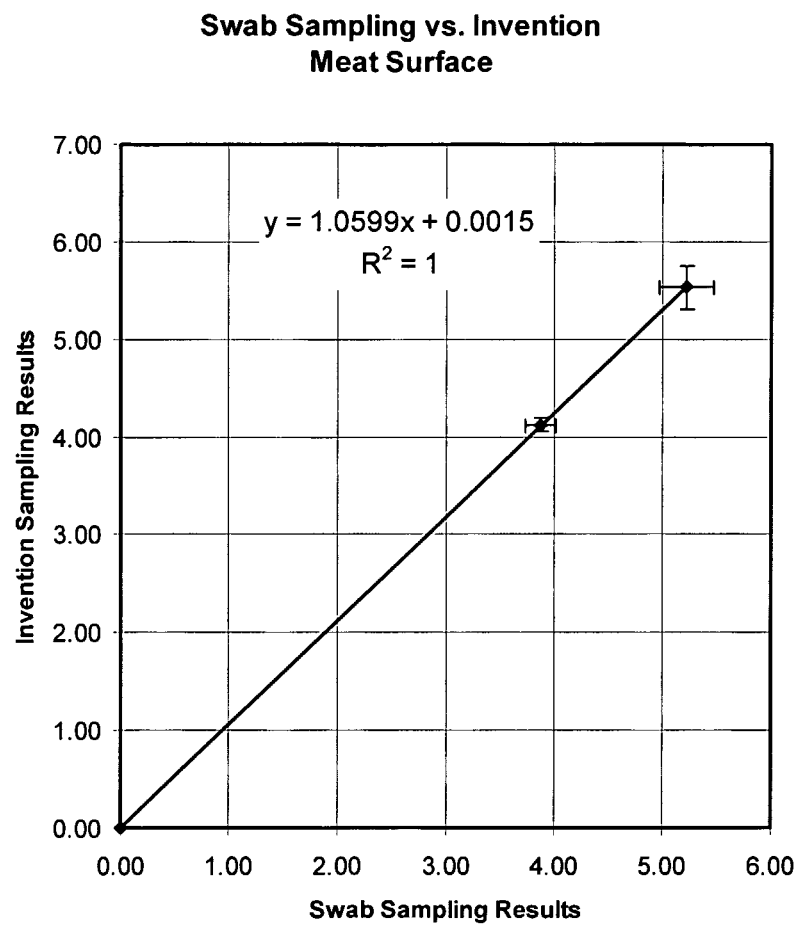
FIG. 4 shows a trend-line comparison of results of sampling of meat surfaces between traditional swab sampling, and sampling according to preferred aspects of the present invention.

The results were analyzed by conducting a 'rend-line' comparison, as shown in FIG. 4. An excellent correlation was observed, with a slope of near unity. Additionally, the inventive apparatus and method showed less variation when sampling this rough surface.

EXAMPLE 2

The apparatus 1 of FIG. 1 was compared to current art-recognized swab sampling for collection of a microbial sample from a hard surface. A FORMICA™ surface was inoculated at two different levels ($10^5$ and $10^4$ CFU/100 cm$^2$) with Biotype I *Escherichia coli* (ECC) prepared from known stock laboratory cultures in slurry of sterilized fecal matter. Surfaces were inoculated by spreading 10 mL of the slurry on a 300 cm$^2$ area of the surface to be sampled, according to the schematic provided in FIG. 3.

Swab samples were collected using sterile sponges moistened with 25 mL of 0.1% peptone water, according to standard methodology recommended by the United States Department of Agriculture (USDA), Food Safety and Inspection Services (FSIS). The apparatus 1 of FIG. 1 was used to collect comparative samples. The sampling fluid reservoir contained 0.1% peptone water, and a volume of approximately 25 mL was applied to the surface while simultaneously using the vacuum to recover the applied fluid. Sampling was done in quintuplicate (n=5). The ECC content of the collected samples was determined through standard serial dilution and plate counting methods. The results obtained with each method are listed below in TABLE 2.

TABLE 2

| Innoculation Level | Formica Hard Surface | |
|---|---|---|
| (CFU/100 sq cm[1]) | Swab Sampling | Invention |
| $10^5$ | 5.27 ± 0.12 | 5.82 ± 0.21 |
| $10^4$ | 4.12 ± 0.07 | 4.21 ± 0.12 |
| 0 | 0 | 0 |

[1]Surfaces were inoculated by spreading 10 mL of a fecal slurry containing the indicated CFU of Biotype I *Escherichia coli* (ECC).
[2]Results are reported as log base 10, plus or minus the standard deviation (n = 5).

Figure 5:
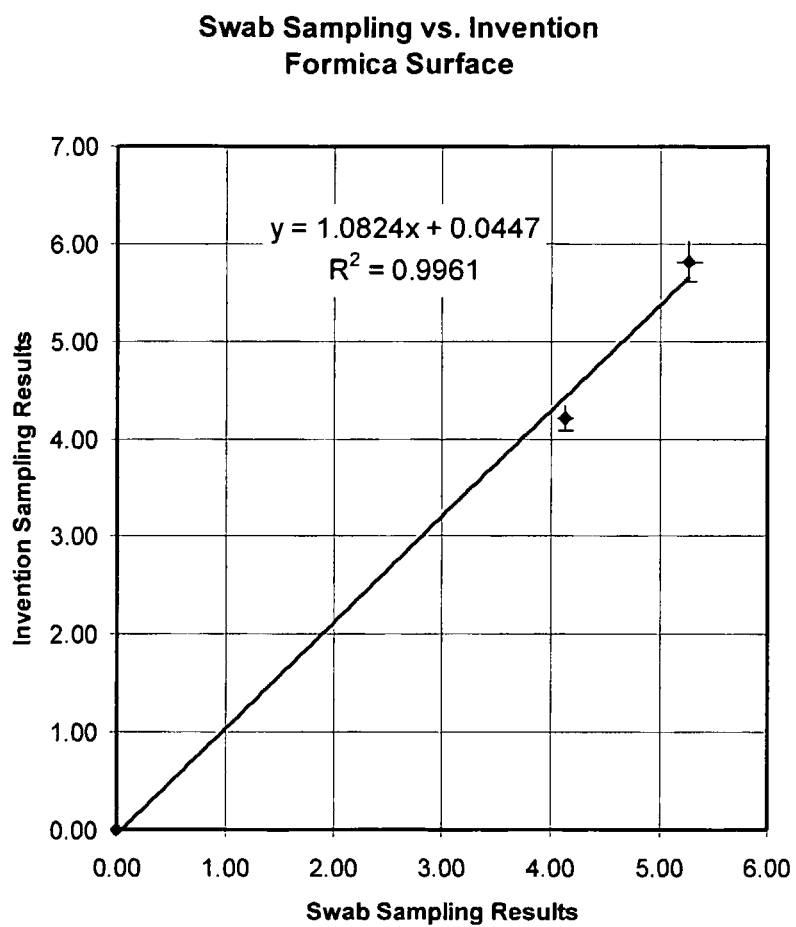
FIG. 5 shows a trend-line comparison between the results of sampling of a FORMICA™ surface using traditional swab sampling, and sampling using preferred aspects of the present invention.

The results were analyzed by conducting a trend-line comparison, as shown in FIG. 5. An excellent correlation was observed, with a slope of near unity, and with a favorable level of variation.

The invention claimed is:

1. An apparatus for sampling microbial organisms present on surfaces, comprising:
   a reservoir suitable for providing microbial collection fluid;
   a sterilizable sample collection chamber;
   a sterilizable, reversibly detachable integrated collection fluid delivery and collection fluid recovery member having a collection fluid delivery channel and a collection fluid recovery channel, and suitable to deliver collection fluid to a target surface, and contemporaneously recover the delivered fluid from the surface;
   a fluid delivery pump, in communication with both the reservoir and the fluid delivery channel of the integrated member, and operable to aseptically deliver collection fluid from the reservoir to the integrated member;
   a vacuum source, in communication with both the sample collection chamber and the collection fluid recovery channel of the integrated member, and operable to direct collection fluid, delivered and recovered by the integrated member, to the sample collection chamber; and
   a sanitizing reservoir for sanitizing the integrated member having the collection fluid delivery channel and the collection fluid recovery channel, said reservoir comprising a heatable sanitizing fluid reservoir configured for receiving the integrated member, and a sanitizer pump configured to provide for circulating sanitizing fluid from the sanitizing reservoir directly to the collection fluid delivery channel or to the collection fluid recovery channel of the integrated member in a closed loop between and through the heated sanitizing fluid reservoir and the collection fluid delivery channel or the collection fluid recovery channel of the integrated member to provide for sanitizing of the integrated member.

2. The apparatus of claim 1, wherein the integrated fluid delivery and recovery member is reversibly detachable.

3. The apparatus of claim 1, wherein the reservoir is a pressurizable chamber.

4. The apparatus of claim 1, wherein the reservoir is a pressurizable chamber, and wherein the delivery pump comprises a compressor in communication with the chamber.

5. The apparatus of claim 1, wherein the delivery pump comprises a fluid pump.

6. The apparatus of claim 1, wherein the vacuum source comprises a vacuum pump, and a moisture trap interposed between the sample collection chamber and the vacuum pump.

7. The apparatus of claim 1, wherein the integrated collection fluid delivery and collection fluid recovery member, comprises a spray nozzle suitable to direct sample collection fluid toward the target surface.

8. The apparatus of claim 1, wherein the integrated collection fluid delivery and collection fluid recovery member comprises a actuatable valve for actuated delivery of the sample collection fluid.

9. The apparatus of claim 1, wherein the integrated collection fluid delivery and collection fluid recovery member conforms to the target surface contour.

10. The apparatus of claim 1, wherein the shape or size of the integrated collection fluid delivery and collection fluid recovery member is calibrated to facilitate sample collection from a predetermined target surface area.

11. A method for rapid, high-throughput sampling of microbial organisms present on surfaces, comprising:
  delivering sample collection fluid to a target surface, and contemporaneously recovering the delivered fluid from the target surface by use of a sterilizable, reversibly detachable integrated collection fluid delivery and collection fluid recovery member having a collection fluid delivery channel and a collection fluid recovery channel;
  collecting the recovered sample collection fluid into a sample collection chamber in communication with the integrated member; and
  sanitizing the integrated member and the collection fluid delivery channel and the collection fluid recovery channel of the integrated member by receiving the integrated member having the collection fluid delivery channel and the collection fluid recovery channel into a heatable sanitizing fluid reservoir and circulating a sanitizing fluid from the sanitizing reservoir directly to the collection fluid delivery channel or to the collection fluid recovery channel of the integrated member in a closed loop between and through the heated sanitizing fluid reservoir and the collection fluid delivery channel and the collection fluid recovery channel of the integrated member to provide for sanitizing of the integrated member between sampling cycles, wherein sample collection is afforded.

12. The method of claim 11, wherein the target surface is a food surface or a food-contact surface.

13. The method of claim 12, wherein the food surface is that of an animal or animal carcass.

14. The method of claim 13, wherein the animal carcass is bovine, porcine, equine or avian.

15. The method of claim 11, wherein the microbial collection fluid preserves microbial vitality without promoting microbial growth, allowing for determination of microbial number per unit surface area.

16. The method of claim 11, wherein the microbial collection fluid promotes microbial growth, allowing for determination of a presence or absence of surface microbial organisms.

17. The apparatus of claim 1, wherein the sterilizable sample collection chamber further comprises a diffuser tube to provide an impinger.

18. A method for rapid, high-throughput atmospheric sampling of microbial organisms, comprising:
  collecting an atmospheric sample by use of a sterilizable, reversibly detachable integrated collection fluid delivery and collection fluid recovery member having a collection fluid delivery channel and a collection fluid recovery channel, the integrated member in communication with a vacuum source;
  directing the collected atmospheric sample into an impinger comprised of a sample collection chamber having a diffuser tube; and
  sanitizing the integrated member and the collection fluid delivery channel and/or the collection fluid recovery channel of the integrated member by receiving the integrated member and the collection fluid delivery channel and the collection fluid recovery channel of the integrated member into a heatable sanitizing fluid reservoir and circulating a sanitizing fluid from the sanitizing reservoir directly to the collection fluid delivery channel or to the collection fluid recovery channel of the integrated member in a closed loop between and through the heated sanitizing fluid reservoir and the collection fluid delivery channel or the collection fluid recovery channel of the integrated member to provide for sanitizing of the integrated member between sampling cycles, wherein atmospheric sampling of microbial organisms is afforded.

* * * * *